United States Patent [19]
Van Der Puy

[11] Patent Number: 4,886,629
[45] Date of Patent: Dec. 12, 1989

[54] PROCESS FOR THE PREPARATION OF FLUORINATED BENZENE SULFONYL FLUORIDES

[75] Inventor: Michael Van Der Puy, Cheektowaga, N.Y.

[73] Assignee: Allied-Signal Inc., Morris Township, Morris County, N.J.

[21] Appl. No.: 203,171

[22] Filed: Jun. 6, 1988

[51] Int. Cl.$^4$ ............................................. C07C 155/00
[52] U.S. Cl. ...................................................... 562/826
[58] Field of Search ..................................... 260/543 F

[56] References Cited

U.S. PATENT DOCUMENTS 3,256,343  7/1966  McCall et al. ...................... 260/612
4,369,145  1/1983  Souler ............................ 260/543 F

FOREIGN PATENT DOCUMENTS 3001896  7/1981  Fed. Rep. of Germany .
3330403  3/1984  Fed. Rep. of Germany .

OTHER PUBLICATIONS

CA 79 (13) 78322g 1973.
CA 71 (19):87914p 1969.
Davies et al., "CCLXXXVI-Aromatic Sulfonyl Fluorides, a Convenient Method of Preparation," J. Chem. Soc. 2104 (1931).
Miller et al., "The Displacement of Aromatic Substituents by Halogen Atoms," J. Am. Chem. Soc. 79, 4187 (1957).
Meerwein et al., Chem. Ber. 10, 841 (1957) Abstract. Chem. Abs. 96:68269g (1982).
Gilbert, "Sulfonation and Related Reactions," Interscience, New York, 1965, pp. 84–87.
Yakobson et al., "Aromatic Fluorine Derivatives", XXIV Fluorine-Containing Benzenesulfonyl Fluorides, J. Gen. Chem. USSR Eng. Trans. 37, 149 (1967).
Blum et al., "Desulfonylation of Aromatic Sulfonyl Halides Catalyzed by Some Platinum-Metal Complexes," J. Org. Chem. 35(6), 1895 (970).
Bianchi et al., "Phase Transfer Catalysis, Preparation of Aliphatic and Aromatic Sulfonyl Fluorides," J. Org. Chem. 42(11), 2031 (1977).
Sekiya et al., "Preparation of Aroyl and Arene Sulfonyl Fluorides from the Corresponding Chlorides using Zinc Fluoride-Pyridine System," Bull. Chem. Soc. Japan 51(4), 1267 (1968).

*Primary Examiner*—Paul J. Killos
*Attorney, Agent, or Firm*—Melanie L. Brown; Jay P. Friedenson

[57] ABSTRACT

The present invention relates to a process for the preparation of a fluorinated benzene sulfonyl fluoride comprising the step of: heating a benzene sulfonyl fluoride of the Formula (I)

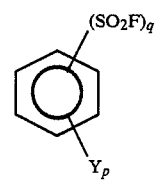

where Y is fluorine, chlorine, bromine, iodine, a methyl group, an ethyl group, or a propyl group; p is 0 to 3; and q is 2 to 6, in the presence of an alkali metal fluoride under conditions and for a time sufficient to provide a fluorinated benzene sulfonyl fluoride of the Formula (II)

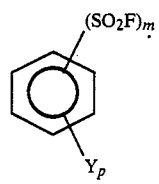

where x is 1 to 5; m=q−x; and Y and p are as defined above.

The present invention also provides novel benzene sulfonyl fluorides of the Formula (III)

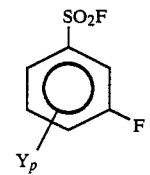

where each Y is meta or para to —SO$_2$F and is independently selected from the group consisting of chlorine, fluorine, fluorosulfonyl, methyl group, ethyl group, and propyl group; and p is 1 or 2.

The fluorinated benzene sulfonyl fluorides are versatile fluorinated intermediates. They are readily converted to sulfonamides of potential activity, or the sulfonyl group can be converted into another functional group, or removed to provide fluorinated benzenes.

5 Claims, No Drawings

PROCESS FOR THE PREPARATION OF FLUORINATED BENZENE SULFONYL FLUORIDES

BACKGROUND OF THE INVENTION

The present invention relates to a process for the preparation of fluorinated benzene sulfonyl fluorides.

The conversion of aryl sulfonyl chlorides or bromides to the corresponding aryl halide proceeds in good yield upon the action of light as taught by Miller et al., "The Displacement of Aromatic Substituents by Halogen Atoms," *J. Am. Chem. Soc.* 79, 4187 (1957); metallic catalysts as taught by U.S. Pat. No. 3,256,343 and Blum et al., "Desulfonylation of Aromatic Sulfonyl Halides Catalyzed by Some Platinum-Metal Complexes," *J. Org. Chem.* 35(6), 1895 (1970); or potassium chloride as taught by Yakobson et al., "Aromatic Fluorine Derivatives, XXIV Fluorine-Containing Benzenesulfonyl Fluorides," *J. Gen. Chem. USSR Eng. Trans.* 37, 149 (1967). Similar conditions for the conversion of aryl sulfonyl fluorides fail entirely or give poor yields.

Consequently, while the conversion of aryl sulfonyl fluorides to aryl fluorides is known, the reaction is not generally reported as being synthetically useful. For example, U.S. Pat. No. 3,256,343 reports the formation of fluorobenzene in 31% yield by passing benzenesulfonyl fluoride over copper on charcoal at 360° C. Blum et al., supra, report the formation of 2-fluoronaphthalene in 10% yield from 2-naphthalenesulfonyl fluoride in the presence of RhCl(PPh$_3$)$_3$ as catalyst. Yakobson et al., supra, report the formation of fluorobenzene in 10% yield from benzenesulfonyl fluoride by reacting with potassium fluoride and state that replacement of a sulfonyl chloride group by chlorine under the action of potassium chloride occurs more readily than the replacement of a sulfonyl fluoride group by fluorine under the action of potassium fluoride.

Ortho- and/or para-fluorinated aryl sulfonyl fluorides are prepared by methods such as fluorine-chlorine exchange reactions on chlorobenzenesulfonyl chlorides or fluorides as taught by U.S. Pat. No. 4,369,145. This method is limited in that chlorine which is meta to a halosulfonyl group may exchange only with difficulty; this is a common situation in aromatic substitution reactions in which the leaving group is meta to the activating group.

Fluorinated aryl sulfonyl fluorides are also prepared by the reaction of fluorobenzenes with chlorosulfonic acid as taught by Gilbert, "Sulfonation and Related Reactions," Interscience, New York, 1965, p. 84–87 or the decomposition of a fluorinated aryl diazonium salt in the presence of sulfur dioxide and hydrogen chloride as taught by Meerwein et al, *Chem. Ber.* 90, 841 (1957), followed by conversion of the fluorinated aryl sulfonyl chloride to fluorinated aryl sulfonyl fluoride. These methods are also limited in that they require expensive fluorobenzene precursors and sulfonation generally occurs para to fluorine, unless another more powerful directing group is present, which may not be desired.

It would be desirable to have an easier process for the preparation of fluorinated benzene sulfonyl fluorides wherein the yield is good and the reactants are less expensive than the reactants required by known processes.

SUMMARY OF THE INVENTION

The present invention provides a process for the preparation of fluorinated benzene sulfonyl fluorides comprising the step of heating a benzene sulfonyl fluoride of the Formula (I)

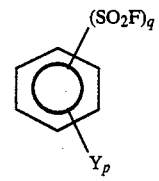

where Y is fluorine, chlorine, bromine, iodine, methyl group, ethyl group, or propyl group; p is 0 to 3; and q is 2 to 6, in the presence of an alkali metal fluoride under conditions and for a time sufficient to provide a fluorinated benzene sulfonyl fluoride of the Formula (II)

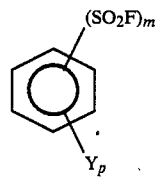

wherein x is 1 to 5; m=q−x; and Y and p are as defined above.

The present process involves a reaction which will be referred to as fluorodesulfonylation. The term "fluorodesulfonylation" as used herein means the replacement of a fluorosulfonyl group with fluorine. Although not wishing to be bound by any theory, it is believed that a nucleophilic aromatic substitution reaction occurs. Fluorodesulfonylation occurs whether the fluorosulfonyl groups of Formula (I) above are ortho, meta, or para to one another so that the present process is free of the difficulties and limitations involved in the processes of U.S. Pat. No. 4,369,145 and the Gilbert and Meerwein et al references as discussed previously.

The present invention also provides novel fluorinated benzenesulfonyl fluorides of the Formula (III)

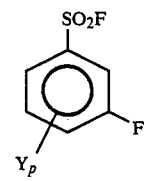

wherein each Y is meta or para to —SO$_2$F and is independently selected from the group consisting of chlorine, fluorine, fluorosulfonyl, methyl group, ethyl group, and propyl group; and p is 1 or 2.

In one embodiment, p is 1 and Y is meta to -F and —SO$_2$F. When Y is fluorine, the present invention provides a compound of the Formula (IV)

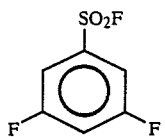

When Y is fluorosulfonyl, the present invention provides a compound of the Formula (V)

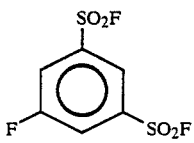

In another embodiment, p is 1 and Y is para to —$SO_2F$. When Y is fluorine, the present invention provides a compound of the Formula (VI)

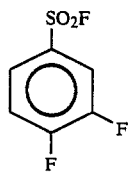

In another embodiment, p is 2 and one Y is para to —$SO_2F$ while the other Y is meta to —F and —$SO_2F$. When the para Y and the meta Y are fluorine, the present invention provides a compound of the Formula (VII)

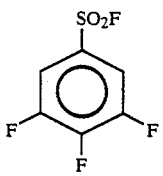

When the para Y is fluorine and the meta Y is chlorine, the present invention provides a compound of the Formula (VIII)

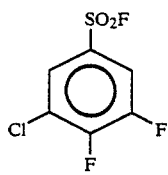

The present process preferably produces
3,5-difluorobenzenesulfonyl fluoride;
5-fluoro-1,3-benzenedisulfonyl fluoride;
3,4-difluorobenzenesulfonyl fluoride;
3,4,5-trifluorobenzenesulfonyl fluoride; and
3-chloro-4,5-difluorobenzenesulfonyl fluoride.

The fluorinated benzene sulfonyl fluorides of the present invention are versatile fluorinated intermediates. For example, they are readily converted to sulfonamides of potential biological activity, or the sulfonyl group can be converted into another functional group, or removed to provide fluorinated benzenes.

As such, the present invention provides a simpler one-step process for the preparation of fluorinated benzene sulfonyl fluorides where the yield is good and the reactants are less expensive than the reactants required by known processes.

Other advantages of the present invention will become apparent from the following description and appended claims.

DETAILED DESCRIPTION OF THE PREFERRED EMBODIMENTS

In the starting benzene sulfonyl fluoride of Formula (I) above, Y may be a substituent selected from the group consisting of fluorine, chlorine, bromine, iodine, a methyl group, an ethyl group, and a propyl group. It should be understood that when Y is chlorine, bromine, or iodine, Y may be readily replaced by fluorine during the present process. Generally, p is about 0 to 3.

Although not wishing to be bound by any theory, it is believed that the fluorosulfonyl group is a good leaving group and a good activating group for a nucleophilic aromatic substitution reaction. As such, q is 2 to 6 in the starting benzene sulfonyl fluoride of Formula (I) above. From a practical standpoint, benzene sulfonyl fluorides having greater than 3 fluorosulfonyl groups are difficult to prepare. Preferably, q is 2 or 3. In the starting benzene sulfonyl fluoride of Formula (I) above, the fluorosulfonyl groups can be ortho, meta, or para to each other. To prepare the novel fluorinated benzene sulfonyl fluorides of Formula (III) above, the starting benzene sulfonyl fluoride of Formula (I) above has at least two fluorosulfonyl groups which are meta to each other.

The benzene sulfonyl fluorides used in the present invention may be prepared by any known method including halogen exchange on the corresponding sulfonyl chlorides by reaction with aqueous sodium or potassium fluoride (Davies et al., "CCLXXXVI-Aromatic Sulphonyl Fluorides—A Convenient Method of Preparation," *J. Chem Soc.* 2104 (1931)), reaction with potassium fluoride in an acetonitrile containing a crown ether (Bianchi et al., "Phase Transfer Catalysis. Preparation of Aliphatic and Aromatic Sulfonyl Fluorides," *J. Org. Chem.* 42, 2031 (1977)), or reaction with anhydrous zinc fluoride in pyridine (Sekiya et al., "Preparation of Aroyl and Arenesulfonyl Fluorides from the Corresponding Chlorides Using Zinc Fluoride-Pyridine System," *Bull. Chem. Soc. Japan* 51(4), 1267 (1978)).

The present invention also provides novel benzene sulfonyl fluorides of the Formula (IX)

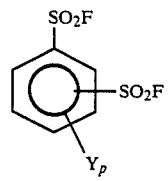

where Y is fluorine or chlorine and p is 0 to 2; the benzene sulfonyl fluorides are useful as starting materials in the present process.

In one embodiment, the second —$SO_2F$ is ortho to the first —$SO_2F$. When p is 0, one novel benzene sulfonyl fluoride is of the Formula (X)

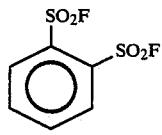

and is prepared by the reaction of 1,2-benzenedisulfonyl chloride with potassium fluoride in an acetonitrile containing a crown ether.

In another embodiment, the second —SO₂F is meta to the first —SO₂F. Preferably, p is 1 or 2 and one Y is ortho to one of the —SO₂F groups and para to the other —SO₂F group. When Y is fluorine and p is 1, another novel benzene sulfonyl fluoride is of the Formula (XI)

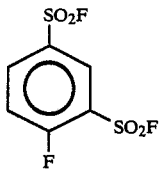

and is prepared by the reaction of 4-fluoro-1,3-benzenedisulfonyl chloride with potassium fluoride in an acetonitrile containing a crown ether.

When Y is chlorine, p is 2, and the second Y is meta to both —SO₂F groups, another novel benzene sulfonyl fluoride is of the Formula (XII)

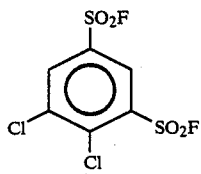

and is prepared by the reaction of 4,5-dichloro-1,3-benzenedisulfonyl chloride with potassium fluoride in an acetonitrile containing a crown ether.

The benzene sulfonyl fluoride of Formula (I) is heated in the presence of an alkali metal fluoride. Useful alkali metal fluorides include sodium fluoride, potassium fluoride, rubidium fluoride, and cesium fluoride. The preferred alkali metal fluoride is potassium fluoride.

Theoretically, only a catalytic amount of alkali metal fluoride is required. Practically, at least one mole of alkali metal fluoride per mole fluorosulfonyl group to be replaced is used. The ratio of alkali metal fluoride to fluorosulfonyl group to be replaced may be used to control the extent of fluorodesulfonylation of a benzene trisulfonyl fluoride. Thus with one equivalent of alkali metal fluoride, only one fluorosulfonyl group is replaced by fluorine; with two equivalents of alkali metal fluoride, two fluorosulfonyl groups are replaced by fluorine.

The process of the present invention may or may not be performed in a solvent with a phase transfer catalyst. If a solvent is to be used, the choice of solvent depends partially on the difference in boiling points of the solvent and the fluorinated benzene sulfonyl fluoride product. If a solvent is to be used, a useful solvent is a relatively inert solvent selected from the group consisting of sulfolane; dimethyl sulfone; dimethyl sulfoxide; N,N-dimethylformamide; N-methylpyrrolidine; benzonitrile, and high boiling glymes. Based on the difference in boiling points of the solvent and the fluorinated benzene sulfonyl fluoride product, generally sulfolane and dimethylformamide are used. When a less polar solvent is used, benefit may be obtained by additionally incorporating a phase transfer catalyst in the reaction medium.

If a solvent is not employed, a phase transfer catalyst may be used. Useful phase transfer catalysts include 18-crown-6, dibenzo-18-crown-6, and quaternary ammonium salts which are stable at the reaction temperature.

The benzene sulfonyl fluoride is heated at a temperature of generally about 50° to 300° C., more specifically about 100° to 280° C., and preferably about 170° to 250° C. The onset of the reaction is indicated by the evolution of sulfur dioxide gas. Separation of the product may be effected by distilling directly from the reaction medium, or by steam distillation followed by distillation or recrystallization.

The present invention is more fully illustrated by the following non-limiting Examples.

Examples 1 to 5 are directed to the preparation of benzene sulfonyl fluorides.

EXAMPLE 1

Preparation of 1,3,5-benzenetrisulfonyl fluoride 1,3,5-Benzenetrisulfonyl chloride (18.9 g, 0.051 mol) was added portionwise over 15 min. to 63.3 g dry pyridine and 16.0 g (0.155 mol) anhydrous ZnF₂ with ice-bath cooling. The mixture was stirred 0.5 h at ice-bath temperature and 1.5 h at room temperature, and then poured slowly into a mixture of 80 mL conc. HCl in 320 mL ice-water. The product was filtered, washed with water, and dried to give 9.1 g solid (55% yield), mp 166°–8° C. Its proton NMR consisted of a singlet at δ 9.1 while the 19F NMR displayed a singlet 65.8 ppm downfield from CFCl₃.

EXAMPLE 2

Preparation of 1,3-benzenedisulfonyl fluoride

A mixture of 25 g 3-fluorosulfonylbenzenesulfonyl chloride (0.097 mol), 0.2 g 18-crown-6, and 10 g (0.172 mol) KF in 75 mL acetonitrile was stirred under N₂ overnight at room temperature. The slurry was filtered and the filtrate evaporated under vacuum. Distillation of the residue gave 21.9 (94%) white solid mp 39°–40° C. (bp 98°–104° C. at 0.5 mm).

EXAMPLE 3

Preparation of 1,2-benzenedisulfonyl fluoride o-Benzenedisulfonyl chloride (prepared from the dipotassium salt according to Hurtley et al., *J. Chem. Soc.*, 1821 (1926) was converted to the corresponding difluoride in 88% yield by stirring 11 g of the disulfonyl chloride, 12.5 g KF, and 0.4 g dibenzo-18-crown-6 in 110 mL CH₃CN for 0.5 h at room temperature. Recrystallization from 60:40 CHCl₃hexanes gave colorless crystals, mp 130°–1° C. 19F NMR: φ 64.5, 1H NMR: AA'BB' pattern at δ 8.1 and 8.5. IR: 1215 cm⁻¹ (—SO₂F). Anal. Calcd. for C₆H₄F₂O₄S₂: C, 29.75%; H, 1.66% Found: C,29.79%; H, 1.63%.

EXAMPLE 4

Preparation of 4-fluoro-1,3-benzenedisulfonyl fluoride

4-Fluoro-1,3-benzenedisulfonyl chloride (24 g, 0.082 mol), 40 g KF, and 0.3 g dibenzo-18-crown-6 were refluxed in 200 mL CH$_3$CN overnight. The mixture was cooled, filtered, and solvent removed by rotary evaporation to give an oil which was distilled under vacuum to give 18.1 g (85%) of the corresponding disulfonyl fluoride, bp 98°–102° C. at 0.05 mm Hg. 1H NMR: δ 8.6 (dd, 1 H), 8.47 (ddd, 1H), 7.7 (t, 1H); 19F NMR: φ 66.0 (s), 63.8 (d), −93.3 (m). Anal. Calcd. for C$_6$H$_3$F$_3$O$_4$S$_2$: C, 27.70%; H, 1.16%. Found: C, 28.03%, H, 1.16%.

EXAMPLE 5

Part A—Preparation of
4,5-dichloro-1,3-benzenedisulfonyl chloride o-Dichlorobenzene (19.5 g), and chlorosulfonic acid (180 mL) were refluxed for 40 h. Work-up gave 29.3 crude product which was recrystallized from hexanes/benzene (100/40) to give pure material (20.5 g), mp 114°–5° C. IR (nujol) 1190 and 1172 cm$^{-1}$ (SO$_2$Cl); 1H NMR δ 8.65 (d, 1 H, J=2 Hz), 8.4 (d, 1H); Anal. Calcd. for C$_6$H$_2$Cl$_4$S$_2$O$_4$: C, 20.95; H, 0.59%, Found: C, 2076; H, 0.55%.

Part B—Preparation of
4,5-dichloro-1,3-benzenedisulfonyl fluoride

The Part A disulfonyl chloride (19.1 g). 19.1 g dry KF, 0.3 g 18-Crown-6, and 125 mL CH$_3$CN were refluxed for 7.5 h. The cooled mixture was filtered and the solvent removed by rotary evaporation. 19F NMR indicated that no ring chlorines had exchanged (singlets at 66.0 and 57.3 ppm downfield from CFCl$_3$). Crude material, containing some residual crown ether, was used in the fluorodesulfonylation described in Example 11.

Examples 6 to 11 are directed to the fluorodesulfonylation of the benzene fluorides prepared according to Examples 1 to 5.

EXAMPLE 6

Fluorodesulfonylation of 1,3,5-benzenetrisulfonyl fluoride, prepared according to Example 1, to yield 3,5-difluorobenzenesulfonyl fluoride 1,3,5-Benzenetrisulfonyl fluoride (8.2 g), 3.0 g KF, and 10 mL sulfolane were heated under N$_2$ for 1.25 h at 190°–210° C. in a flask fitted with a short path distillation take-off head. During this time, gas was evolved. The product was distilled directly at 20 mm Hg to give 2.4 g (49%) colorless liquid boiling at 78°–80° C. 1H NMR(CDCl3): δ 7.6 (m, 2H), 7.25 (tt, 1H); 19F NMR: φ 64.5 (s, 1 F), −103.7 (m, 2F); IR: 3105, 1610, 1450, 1420, 1310, 1215, 1135, 1090, 995, 900, 870, 775, 665, and 610 cm$^{-1}$; MS m/e 196 (parent), 113 (base). Anal. Calcd. for C$_6$H$_3$F$_3$O$_2$S: C, 36.74; H, 154; found: C, 36.55; H, 1.66.

EXAMPLE 7

Fluorodesulfonylation of 1,3,5-benzenetrisulfonyl fluoride, prepared according to Example 1, to yield 5-fluoro-1,3-benzenedisulfonyl fluoride A mixture of 1.60 g 1,3,5-benzenetrisulfonyl fluoride, 0.19 g KF, and 0.05 g dibenzo-18-crown-6 were heated under N$_2$ for 20 min at 200° C. During this time, gas evolution was rapid during the first 10 minutes. The product was distilled directly from this mixture; bp 88° C. at 0.45 mm Hg (0.82 g, 65%). 1H NMR (CDCl3) δ 8.43 (s, 1H), 8.1 (dd, 2 H); 19F NMR 65.3 (s, 2F), −101.3 (t, 1F); IR (neat) medium and strong bands at 3100, 1610, 1450, 1425, 1272, 845, 790, 770, 665, and 620 cm$^{-1}$. Anal. Calcd, for C$_6$H$_3$F$_3$S$_2$O$_4$: C, 27.70%, H, 1.17%; Found: C, 28.04%, H, 1.25%.

This example illustrates that less than one mole of alkali metal fluoride per mole fluorosulfonyl group to be replaced may be used.

EXAMPLE 8

Fluorodesulfonylation of 1,3-benzenedisulfonyl fluoride, prepared according to Example 2, to yield 3-fluorobenzenesulfonyl fluoride 1,3-Benzenedisulfonyl fluoride (14.5 g, 0.06 mol), 7.8 g KF, and 10 mL sulfolane were heated under N$_2$ for 4.75 h at 235°–242° C. The mixture was cooled and diluted with 100 mL CH$_2$Cl$_2$ and 100 mL water. The organic layer was separated and the aqueous portion extracted with CH$_2$Cl$_2$. The combined organic layers were distilled, the product being collected at 92°–101° C. at 20 mm. Yield: 4.8 g (45%). 19F NMR 64.5 (s, 1 F), −107.7 ppm (dt, 1 F). Sulfonamide, mp 129°–131° C.

EXAMPLE 9

Fluorodesulfonylation of 1,2-benzenedisulfonyl fluoride, prepared according to Example 3, to yield 2-fluorobenzenesulfonyl fluoride o-Benzenedisulfonyl fluoride (6.3 g, 26 mmol), 2.0 g KF, and 6 mL sulfolane were heated under N$_2$ for 45 min. at 200°–215° C. The condenser was replaced with a short vigreux column, and the product distilled directly from the reaction mixture yielding 3.7 g (80%) colorless liquid, bp 90–94 at 10 mm. 19F NMR: φ 63.3 (d, J=12 Hz, 1 F), −106.7 (m, 1F). MS (m/e) 178 (parent and base).

EXAMPLE 10

Fluorodesulfonylation of 4-fluoro-1,3-benzenedisulfonyl fluoride, prepared according to Example 4, to yield 3,4-difluorobenzenesulfonyl fluoride This material was prepared from 4-fluoro-1,3-benzenedisulfonyl fluoride in a manner similar to that described above for 3-fluorobenzenesulfonyl fluoride in Example 8. 50% yield. Bp 72° C. at 8 mm. 1H NMR: δ 7.3–7.6 (1H), 7.7–8.0 (2H); 19F NMR: φ 65.5, −123.7, and −131.3. There was no evidence of 2,5-difluorobenzenesulfonyl fluoride as a reaction product.

EXAMPLE 11

Fluorodesulfonylation of 4,5-dichloro-1,3-benzenedisulfonyl fluoride, prepared according to Example 5, to yield 3-chloro-4,5-difluorobenzenesulfonyl fluoride Crude 4,5-dichloro-1,3-benzenedisulfonyl fluoride (19.0 g) was heated in 65 mL DMF containing 10 g KF to reflux over a period of 30 min, and held at reflux for an additional 45 min. The mixture was cooled, poured into 400 mL water, and extracted with ether. The combined ether extracts were washed with water, brine, and dried over MgSO$_4$. After removing the ether, the residue (10.4 g) was distilled under vacuum. The fraction boiling at 71°–86° C. (7.2 g) contained 5–10% 3,4,5-trifluorobenzenesulfonyl fluoride (GC-MS m/e 214 (parent); 19F NMR showed aromatic fluorine at −127.2 (dd) and −146 (tt)). Pure (97%) 3-chloro-4,5-difluorobenzenesulfonyl fluoride was obtained by redistillation (bp 78°–80° C. at 4 mm Hg). GC-MS m/e 230 (P), P+2 approx. 30% of P, 135 (base); 19F NMR 65.8

(s), −124.1, −128.2. Anal. Calcd. for C6H2ClF3O2S: C, 31.25; H, 0.87; Found: C, 30.88; H. 0.87%.

Having described the invention in detail and by reference to preferred embodiments thereof, it will be apparent that modifications and variations are possible without departing from the scope of the invention defined in the appended claims.

What is claimed is:

1. A process for the preparation of a fluorinated benzene sulfonyl fluoride comprising the step of:

heating a benzene sulfonyl fluoride of the Formula

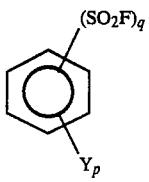

where Y is fluorine, chlorine, bromine, iodine, a methyl group, an ethyl group, or a propyl group; p is 0 to 3; and q is 2 to 6, in the presence of an alkali metal fluoride under conditions and for a time sufficient to provide a fluorinated benzene sulfonyl fluoride of the Formula

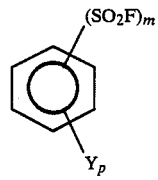

wherein x is 1 to 5; m=q−x; and Y and p are as defined above.

2. The process of claim 1 wherein said alkali metal fluoride is an alkali metal fluoride selected from the group consisting of sodium fluoride, potassium fluoride, rubidium fluoride, and cesium fluoride.

3. The process of claim 1 wherein said alkali metal fluoride is potassium fluoride.

4. The process of claim 1 wherein said q is 2 or 3.

5. The process of claim 4 wherein at least two of said —SO₂F groups are meta to each other.

* * * * *

UNITED STATES PATENT AND TRADEMARK OFFICE
CERTIFICATE OF CORRECTION

PATENT NO. : 4,886,629

DATED : December 12, 1989

INVENTOR(S) : Van Der Puy

It is certified that error appears in the above—identified patent and that said Letters Patent is hereby corrected as shown below:

In the Abstract

Formula (II)

delete

"
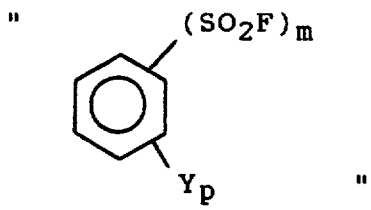
"

substitute therefor

--'
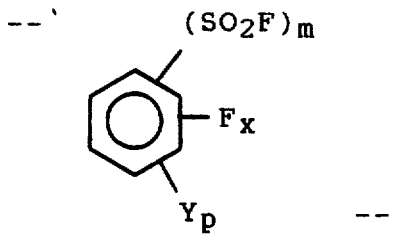
--

UNITED STATES PATENT AND TRADEMARK OFFICE
CERTIFICATE OF CORRECTION

PATENT NO. : 4,886,629
DATED : December 12, 1989
INVENTOR(S) : Van Der Puy

It is certified that error appears in the above-identified patent and that said Letters Patent is hereby corrected as shown below:

In the Specification

Column 2, line 27 delete

"  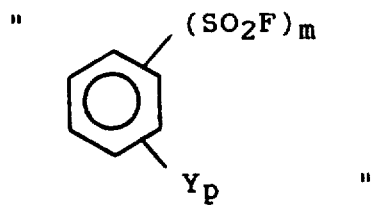  "

substitute therefor

--  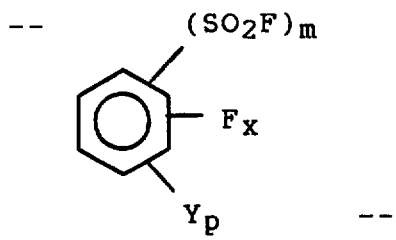  --

UNITED STATES PATENT AND TRADEMARK OFFICE
CERTIFICATE OF CORRECTION

PATENT NO. : 4,886,629  Page 3 of 4
DATED : December 12, 1989
INVENTOR(S) : Van Der Puy It is certified that error appears in the above-identified patent and that said Letters Patent is hereby corrected as shown below:

<u>In the Claims</u>

Column 10, claim 1, line 7 delete

"  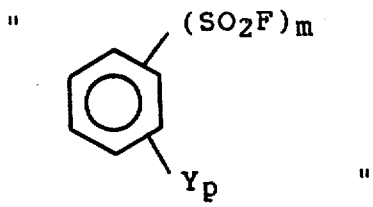  "

UNITED STATES PATENT AND TRADEMARK OFFICE
CERTIFICATE OF CORRECTION

PATENT NO.  : 4,886,629

DATED       : December 12, 1989

INVENTOR(S) : Van Der Puy

It is certified that error appears in the above-identified patent and that said Letters Patent is hereby corrected as shown below:

substitute therefor

-- 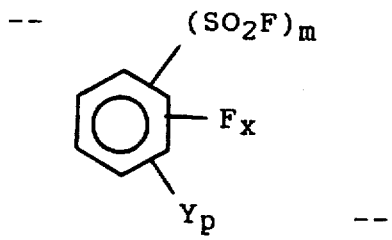 --

Signed and Sealed this

Ninth Day of October, 1990

*Attest:*

HARRY F. MANBECK, JR.

*Attesting Officer*   *Commissioner of Patents and Trademarks*